United States Patent [19]
Habib

[11] Patent Number: 5,372,573
[45] Date of Patent: Dec. 13, 1994

[54] BLOOD FLOW
[75] Inventor: Nagy A. Habib, Ealing, England
[73] Assignee: British Technology Group Limited, London, England
[21] Appl. No.: 834,286
[22] PCT Filed: Jun. 19, 1990
[86] PCT No.: PCT/GB90/00942
  § 371 Date: Feb. 20, 1992
  § 102(e) Date: Feb. 20, 1992
[87] PCT Pub. No.: WO90/15630
  PCT Pub. Date: Dec. 27, 1990
[30] Foreign Application Priority Data
  Jun. 20, 1989 [GB] United Kingdom ............ 8914127.9
  Jun. 26, 1989 [GB] United Kingdom ............ 8914620.3
[51] Int. Cl.⁵ ............................................. A61M 1/12
[52] U.S. Cl. ................................... 600/16; 623/3
[58] Field of Search ............... 600/16, 17, 18; 623/3
[56] References Cited

U.S. PATENT DOCUMENTS

| | | | |
|---|---|---|---|
| 3,518,033 | 6/1970 | Anderson | 600/16 |
| 3,885,251 | 5/1975 | Pedroso | 3/1 |
| 4,014,318 | 3/1977 | Dockum et al. | 600/16 |
| 4,794,910 | 1/1989 | Mushika | 600/18 |

FOREIGN PATENT DOCUMENTS

| | | |
|---|---|---|
| 0192574 | 7/1986 | European Pat. Off. |
| 0217964 | 4/1987 | European Pat. Off. |
| 0209070 | 7/1987 | European Pat. Off. |
| 7407385 | 3/1974 | France |
| 2387041 | 11/1978 | France |
| 3538718A1 | 4/1987 | Germany |
| WO80/02366 | 12/1980 | WIPO |

Primary Examiner—William E. Kamm
Assistant Examiner—Kennedy J. Schaetzle
Attorney, Agent, or Firm—Nixon & Vanderhye

[57] ABSTRACT

A provision of improving the flow of blood through a region of increased impedance is disclosed. The provision comprises assisting blood flow is said region by means of a pump placed in or around a blood vessel supplying blood to said area, and acting to pump blood in the required direction. The pump (1) comprises, in one embodiment, a housing (2) annularly surrounding a compressible conduit (3), said housing (2) containing a plurality of flexible inflatable containers (4) mounted for contact with said conduit (3) (e.g. a blood vessel) and means for effecting sequential inflation and deflation of said containers (4) so as to create a peristaltic pumping effect.

27 Claims, 14 Drawing Sheets

UNIT AT REST

PHASE 0-UNIT AT REST INSTALLED AROUND THE PORTAL VEIN

PHASE 1 STATE 1
BALLONETS UNDER PRESSURE

PHASE 1 STATE 0
BALLONETS UNDER DEPRESSION $R_{Hep}$ HEPATIC RESISTANCE $R_{Hep}$ HEPATIC RESISTANCE

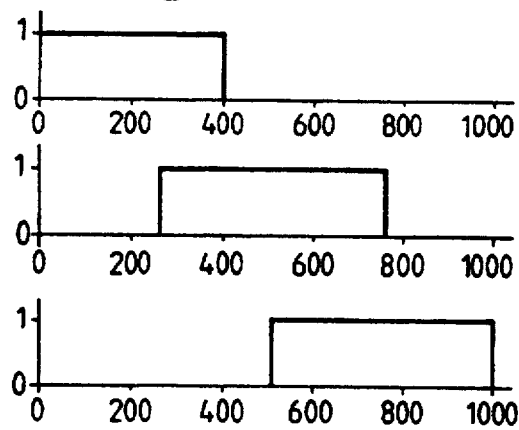
Fig. 8(a)
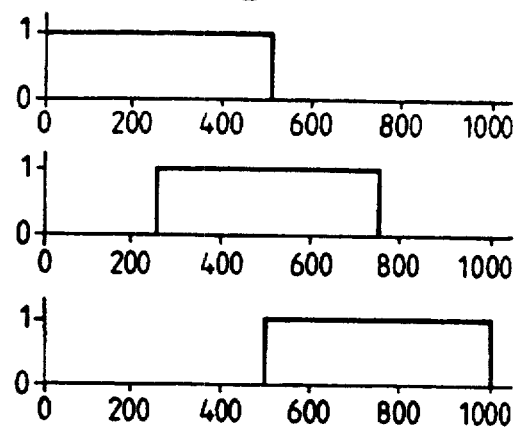
Fig. 8(b)
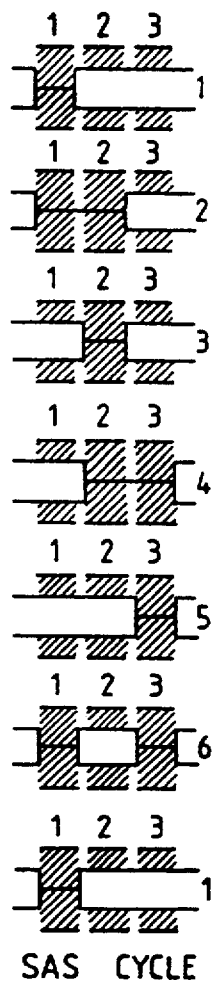
SAS CYCLE
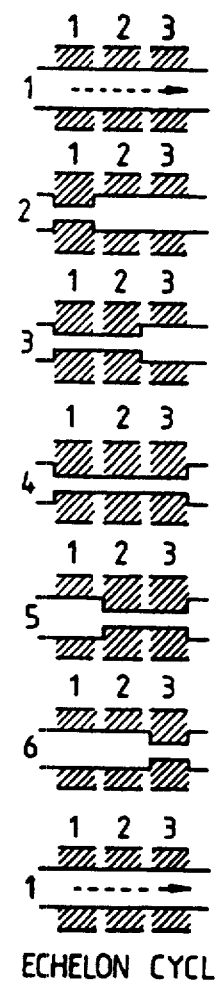
ECHELON CYCLE

PHASE 0          PHASE 1

$R_{Hep}$ HEPATIC RESISTANCE     $Q_{vp}$ PORTAL OUTPUT
$R_c$ COLLATERAL RESISTANCE     $Q_{ve}$ COLLATERAL OUTPUT $Q_{vs}$ SPLANCHNIC GLOBAL OUTPUT IDENTICAL TO PHASES 0 & 1

BLOOD FLOW

This invention relates to techniques and apparatus for improving blood flow in vivo. The invention finds application in both clinical and veterinary practice.

Numerous problems arise from localised impedance to blood flow in both humans and non-human animals. For example, arterial damage, e.g. atherosclerosis, in the leg often requires complex surgery in which, typically, the long saphenous vein is used as a graft to by-pass the non-functional arterial region. Also, cirrhosis of the liver, which may result from alcohol abuse in the western world but which is widespread in the third world as a result of vital hepatitis, results in an impedance to blood flow from the hepatic portal vein into the liver. This results in blood by-passing the liver through portal vein tributaries which feed into the stomach. This results in bleeding from the stomach wall (i.e. oesophageal varices).

The conventional treatment for this condition takes several forms: the blood pressure may be relieved by surgically forming a porto-systemic shunt such as a porto-caval shunt, in which the portal vein is connected to the vena cava; or sclerotherapy may be used, in which the portal vein tributaries are closed off by an appropriate injection. Other conventional treatments are oesophageal transaction, in which the portal vein tributaries are closed off by appropriate sutures; and liver transplantation. These various treatments have various advantages and disadvantages and, in some circumstances, may be of limited value. Sclerotherapy and oesophageal transection may not be effective over a long period of time because the portal pressure (i.e. the blood pressure in the portal vein) is not reduced and often causes a recurrence of bleeding, and a porto-caval shunt leads to most of the products absorbed by the gastro-intestinal tract passing directly into the general blood circulation, instead of travelling first to the liver where extensive metabolic processes, in particular detoxification processes, take place. This decrease in blood flow through the liver reduces the effectiveness of this organ, particularly in its detoxifying capacity. This in turn can lead to serious side effects such as hepatic encephalopathy.

It will be appreciated from the above examples that standard treatment for a localised impedance to blood flow is to provide some means whereby blood can by-pass the obstruction, thereby removing the localised hypertension, or to replace the diseased segment as in liver transplantation.

The present invention proceeds from the realisation that this standard approach is flawed. In many clinical or veterinary conditions demonstrating localised blood flow impedance, we believe that superior results may be achieved if instead of providing a surgical by-pass or other conventional treatment, means are adopted whereby blood flow is assisted through the area of impedance. This will generally result in localised hypertension, but the effects of this will not be felt systemically. Replacing the diseased vessel containing the vascular imbalance (liver transplantation) is not a practical proposition on a large scale because of the high cost of this procedure and because of the limited availability of donors.

According to one aspect of the present invention, there is provided a method of improving the flow of blood through a region of increased impedance, which comprises assisting blood flow in the said region by means of a pump placed in or around a blood vessel supplying blood to said area, and acting to pump blood in the required direction.

The pump may be, for example, an Archimedes screw which acts directly on the blood flowing within the vessel undergoing treatment, or it may be a peristaltic-type pump which acts on the outside of the vessel.

The invention will be described further with reference to treatment of the portal vein or hepatic pedicle (free edge of the lesser ormentum) to overcome problems arising from cirrhosis of the liver, although it is to be understood that the invention is of general applicability and is not restricted to this specific area of treatment.

The pump for use in this embodiment of the present invention can be located internally within the portal vein, or it may be of a type (e.g. a peristaltic pump) which permits the motor to act on the exterior of the blood vessel, thereby avoiding the need to perform surgery on the vessel itself. Examples of suitable pumps will now be given.

In one arrangement, the pump is in the forth of an Archimedes screw which is located within a suitable prosthesis, e.g. one made of Dacron, which is inserted into or grafted between sections of the portal vein. Control of the screw can be achieved by means of a microprocessor housed under the skin close to the site of the portal vein, or located externally in a suitable housing which will generally be held close to the body in the region of the portal vein. A pressure sensor may be incorporated in the screw pump, at the upstream end thereof, and may be incorporated into the control system; for example, the sensor can be used to ensure that the pressure in the portal vein is not greater than 15 mm Hg. In order to avoid complications arising from thrombosis, the administration of an anticoagulant may be desirable with this arrangement.

A peristaltic pump acting on the outside of the hepatic portal vein is advantageous in that its use requires less invasive surgery than the embodiment described above. In one arrangement, a conventional roller action is used to generate the peristaltic effect. As with the embodiment described above, control of the pump may be achieved electrically using an externally located microprocessor.

An alternative peristaltic-type pump is also advantageous; this uses hydraulic or pneumatic power to generate the required peristaltic action, and as above it can be controlled by an externally located microprocessor. One arrangement of this type utilises an annular sheath which conveys a compressive force along its length to assist blood flow within the vessel.

One embodiment of the peristaltic type comprises a jacket, sheath or collar which, in use, surrounds the portal vein. In another embodiment, the peristaltic pump comprises a plurality of inflatable members which are arranged to overlie the vessel or to sandwich it between them. In both embodiments, the device is advantageously under control of, for example, a microprocessor. The fluid supply is preferably a pneumatic supply, and can be provided via an air compressor located outside the body of the patient. This may be at skin level close to the portal vein. A pressure sensor is preferably located on the surface of the portal vein and is linked to the microprocessor. When the pressure in that part of the portal vein between the pump and the liver exceeds 15 mm Hg, the microprocessor will activate the air compressor and the pneumatic pump action.

This will decrease the pressure within the part of the portal vein between the intestine and the pump, which in turn results in cessation of bleeding from the oesophageal varices. Also, the pressure in the section of the portal vein between the device and the liver is increased, thus leading to increased blood flow into the cirrhotic liver despite the high resistance to blood flow. This in turn should assist in the detoxification of blood before gastro-intestinal products reach the systemic blood supply, thereby leading to an improvement in, or prevention of, hepatic encephalopathy.

According to a second aspect of the present invention, there is provided a pump adapted, at least by way of dimensioning and/or flow performance characteristics, for use in or around the hepatic portal vein to improve the flow of blood therethrough against increased impedance caused by abnormality of the liver.

According to a third aspect of the present invention, there is provided the use of a pump, locatable in or around a blood vessel, in the manufacture of a product for application in surgery to treat conditions characterised by impeded flow of blood through the liver.

Preferably, the blood vessel is the hepatic portal vein. Such a pump may comprise a housing for annularly surrounding the hepatic portal vein, said housing containing a plurality of flexible inflatable containers mounted for contact with the hepatic portal vein and means for effecting sequential inflation and deflation of the containers so as to create a peristaltic pumping effect.

Preferably, a device of the type just described is divided into at least two, and typically three annular segments or digitate elements each of which has its own pneumatic supply, and is under individual control from, for example, a microprocessor.

The jacket may be formed of two linked semilunar cusps which can be tied at their edge to form an oblate cylindrical jacket which surrounds the ovoid section of the portal vein. Such a shape is advantageous in that pressure pulses applied via the jacket to the portal vein tend to compress the two "sides" of the ovoid vein evenly. Also, application of the jacket to the portal vein at the free edge of the lesser ormentum is surgically very simple, as opposed to individual dissection of the portal vein. Preferably, the exterior surface of such a jacket is semi-solid, preferably silastic; and the inner surface (which contacts the external wall of the portal vein in use) is membranous so as not to damage the tissue of the portal vein.

Where the jacket comprises three segments or elements, these can be controlled so that each acts as a valve, permitting blood to flow in one direction only. The three segments will be arranged to act sequentially in a predetermined manner so as to massage the portal vein on order to direct blood unidirectionally towards the liver. A variety of segmental configurations and control arrangements are possible. For example, all three segments may be substantially identical; or the middle segment may be the largest. The control system either inflates or deflates the segment (or cuff) to give the required control. It is presently envisaged that a blood flow of up to 1.8 liter per minute from the portal vein into the liver should be possible by means of such a device. This may be contrasted with situations where, as a result of severe cirrhosis, blood flow through the liver is actually reversed.

A presently preferred arrangement utilises three segments all of which are of the same size. An operating sequence for such a three-segment jacket is as follows, segment 1 being the most distal and segment 3 the most proximal with respect to the liver (i.e. segment 1 being downstream and segment 3 being upstream with respect to the direction of flow of blood towards the liver):

| Segment | Time | | | | |
|---|---|---|---|---|---|
|  | $t_1$ | $t_2$ | $t_3$ | $t_4$ | $t_5$ |
| 1 | I | I | D | D | I |
| 2 | D | I | I | D | D |
| 3 | D | D | I | D | D | where I=inflated, and D=deflated. Other sequences are possible, provided that unidirectionality of blood flow is maintained. The same sequence may be used with three digitate elements instead of three annular cuffs.

It will thus be seen that compartment 1 (the distal segment) acts as a valve which allows blood to flow only towards the liver. When this segment is inflated, the desired pumping action is achieved by inflating the central segment (segment 2) while the proximal segment 3 is still deflated. This action pumps blood towards the liver. Next, segment 3 is inflated- Then all three segments are deflated, after which segment 1 is inflated while segments 2 and 3 are deflated, thus priming the pump for the next cycle. Since a device of this type involves minimal surgical intervention, and does not involve any direct contact with the blood, the use of anticoagulants may not be needed.

It is envisaged that such a three-compartment jacket may be controlled so as to undergo about 60 cycles per minute, although it is preferred that the pressure of operation and the frequency of operation be under microprocessor control. A device in accordance with this invention may also include one or more pressure sensors associated (in use) with the portal vein. Such sensors may be used to supply information to the microprocessor which then controls the operation of the device in accordance with prevailing pressure conditions in the portal vein.

A pneumatically operated embodiment such as that described above may have air supply lines for each segment of the jacket which pass through the body of a patient to the exterior, where they are connected to an air compressor. Since the jacket is entirely closed, there is no need to use purified air; the compressor can simply take ambient air and feed this into the segments of the jacket.

A further feature of pneumatically operated jackets such as just described is that operation of the jacket can be aborted in an emergency simply by cutting the air supply line(s) from the compressor. This represents a considerable safety feature. Also, a sudden decrease in pressure in any one segment (which might be due to perforation of the segment) wall lead to stoppage of the pump. Immediate cessation of pump action in such circumstances will prevent air being introduced into the peritoneal cavity.

In a further embodiment, a section of the portal vein is removed and is replaced by a jacket which may be in the form described above with reference to an externally applied jacket. Alternatively, a single compartment annular prosthesis with a single air supply line may be used, but in conjunction with one-way valves at both ends of the jacket. With this arrangement, injection of air pumps blood forwards into the liver, and deflation allows blood to flow into the device from the section of the portal vein between the intestine and the device. Because there is direct contact between the device and the blood, the use of an anticoagulant is preferred with this arrangement.

A device in accordance with this invention may be used by a patient continuously or intermittently; it may sometimes be advantageous to operate the device for a period of, say, two, four or eight hours in every twentyfour. In any case, such aspects will be decided in accordance with advice from the patient's surgeon. Clinical considerations will also be used to determine whether the device is left in situ and used as and when required (both in relation to a diurnal operating regime and in relation to longer term usage, e.g. operation of the device for four hours in every twentyfour for a period of fourteen days, followed by seven days without use). It may also be feasible to remove the device after a course of treatment, and to re-apply the device at a later date in the event of regression.

In one embodiment, the device uses a microprocessor and two pressure sensors to control its functioning. One sensor is located so as to sense the prevailing pressure in that segment of the portal vein between the device and the intestines; and the second sensor so as to sense the pressure prevailing in that segment of the portal vein between the device and the liver. For example, if the pressure sensed by the first sensor exceeds 15 mm Hg, the microprocessor will actuate the device; when this pressure falls below 15 mm Hg, the microprocessor will stop the pump action of the device. Similarly, if the pressure sensed by the second sensor (between the device and the liver) exceeds 100 mm Hg, the microprocessor will respond by switching off the pump action of the device, thereby overriding the control command resulting from the output of the first sensor. This will prevent unacceptably high pressures in the portal vein segment leading to the liver. Functioning of the pump device will then be restored when the pressure sensed by the second sensor falls below 100 mm Hg, provided that the pressure sensed by the first sensor exceeds 15 mm Hg. It will be appreciated that the pressure given above are by way of example only; the device of this invention is preferably arranged so that it can be programmed to respond to any desired limiting pressures in accordance with the surgeon's judgement.

This invention is expected to find application in other clinical or veterinary conditions involving increased impedance to blood flow, e.g. cardiac ischaemia and atherosclerosis of the renal artery, as well as ischaemia of the limbs and brain, and pulmonary hypertension. It may also find use in the relief of ascites.

The action of the pump on the hepatic portal vein or hepatic pedicle (free edge of the lesser ormentum) in accordance with one aspect of this invention will cause a reduction in portal pressure and hence is likely to relieve oesophageal varices. This reduction in portal pressure may also decrease bleeding in the splanchnic territory, which could be an advantage in intestinal surgery.

For a better understanding of the invention and to show how the same may be carried into effect, reference will now be made, by way of example only, to the accompanying drawings, in which:

FIGS. 1a to c show a pump in accordance with the invention;

FIGS. 2.a to d show the constriction and dilation of the portal vein by a single active unit;

Figure 10:
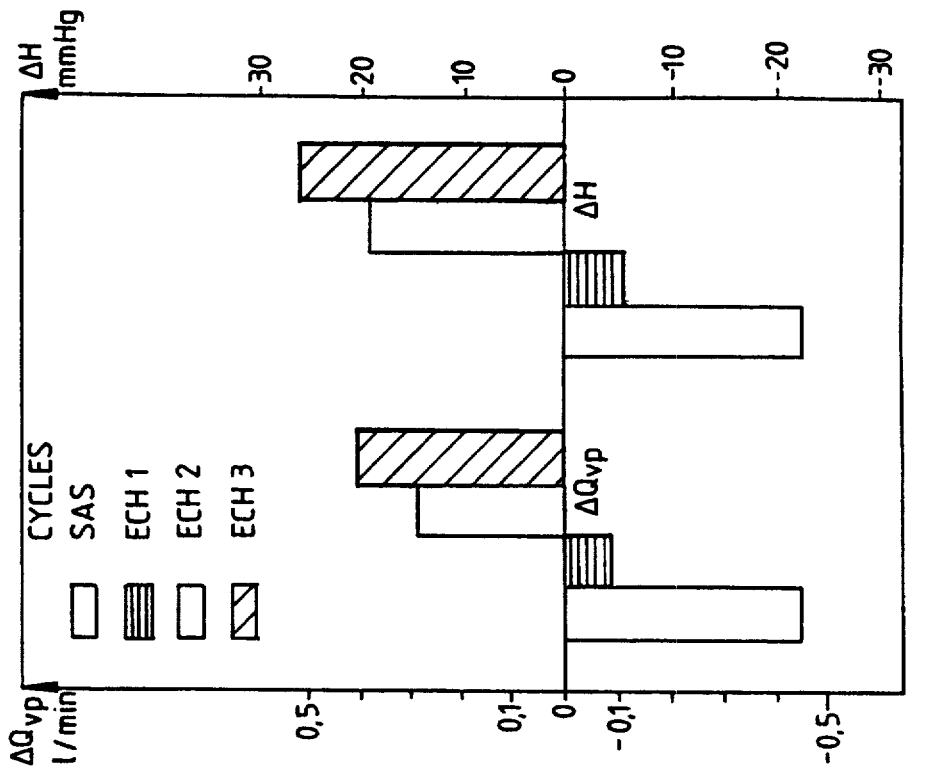
Figure 10:
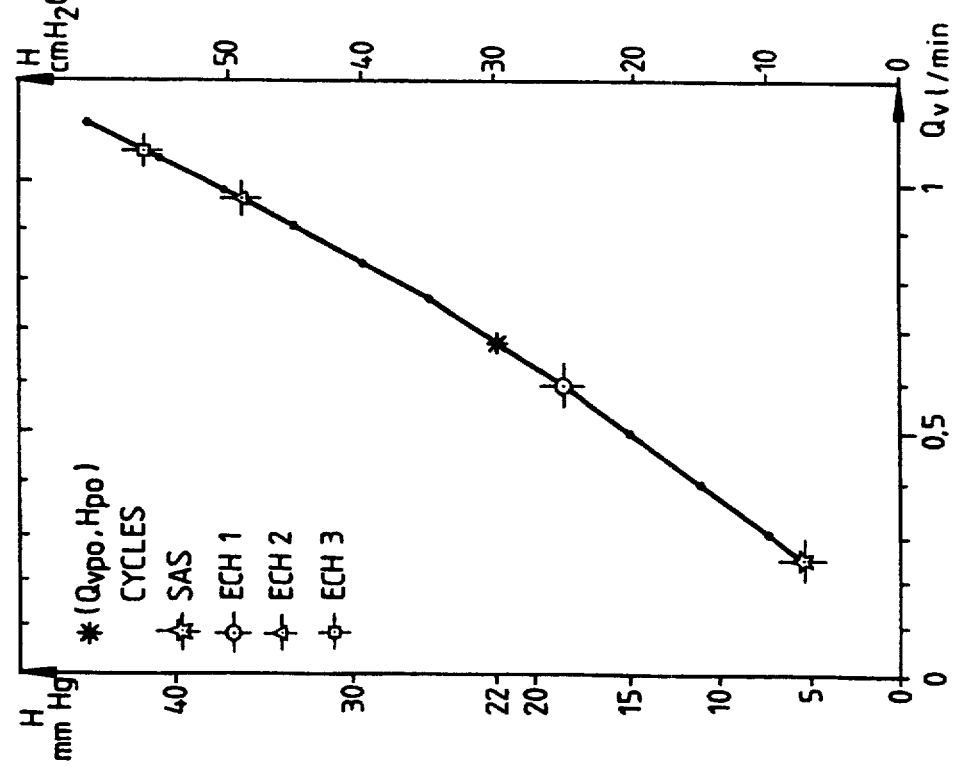
Figure 11:
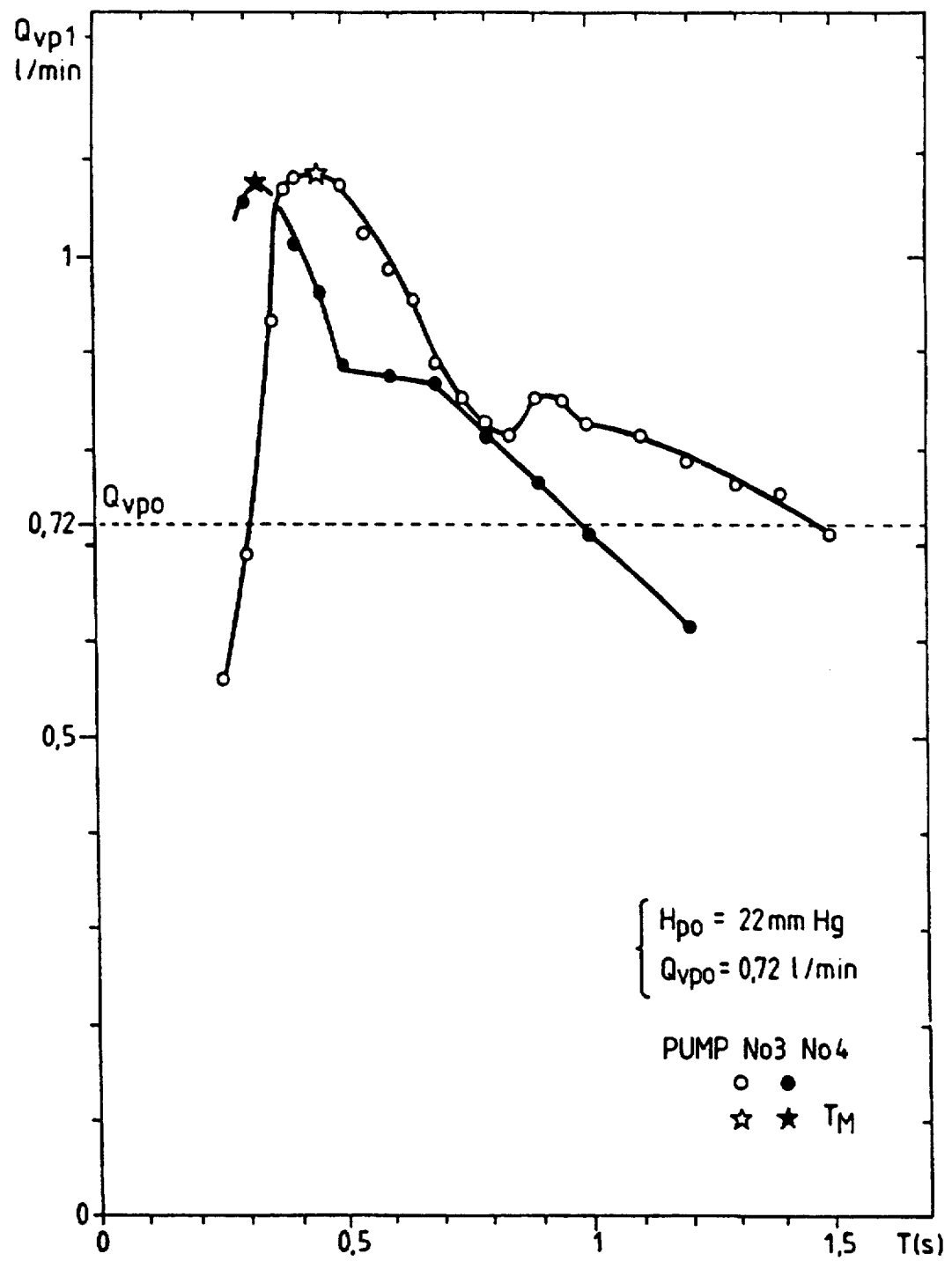
Figure 12A:
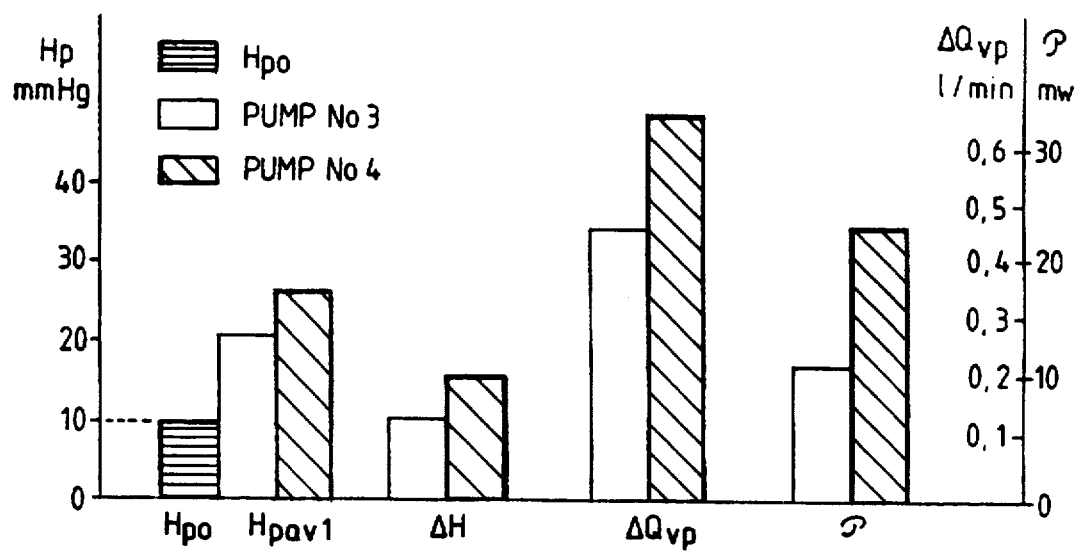
Figure 12B:
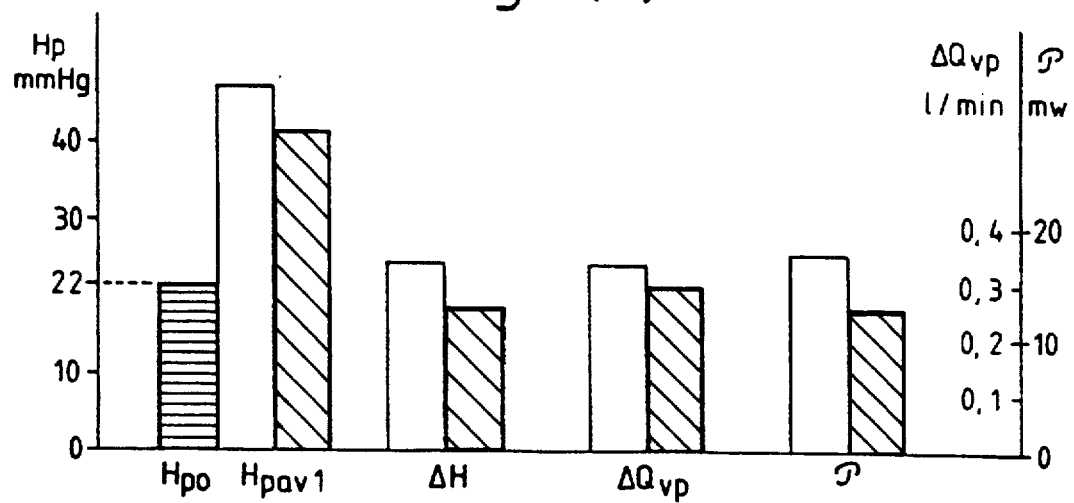
Figure 13:
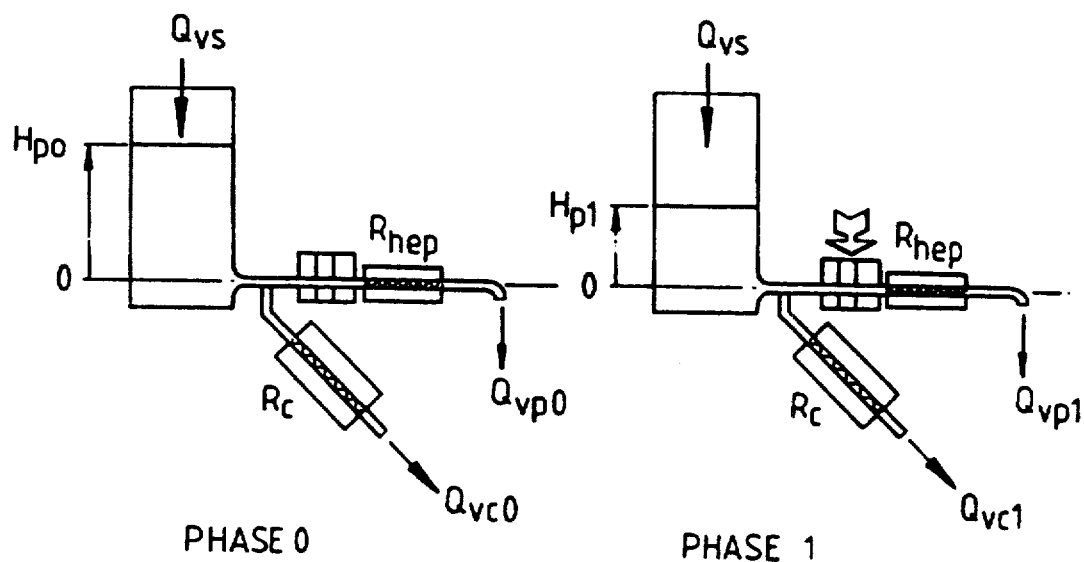
Figure 14A:
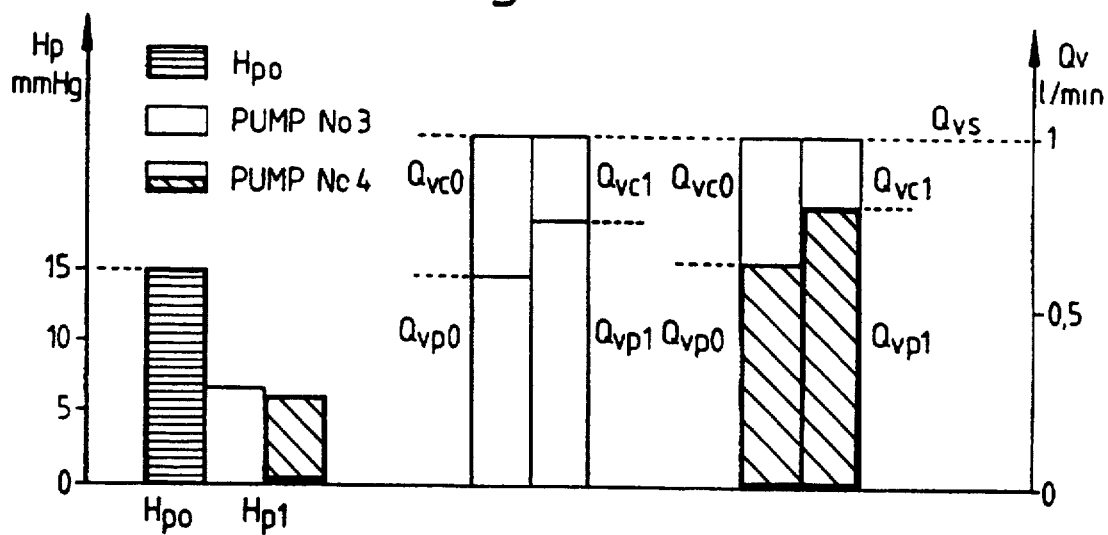

FIGS. 8a and b show chronographs and sequences of pressurisation and relaxation of the SAS and ECHELON type cycles;

FIGS. 9a through d show chronographs of the SAS type cycle and three ECHELON type cycles tested on two pumps in accordance with one aspect of the invention;

FIGS. 10a and 10b are diagrams showing a comparison of the performances of the SAS, ECH1, 2 and 3 cycles when tested on a pump in accordance with one aspect of the invention;

FIG. 11 is a graph showing period of cycle against output for the two pumps tested;

FIGS. 12a and b are diagrams showing comparative performances of the two pumps tested;

FIG. 13 is a diagrammatic representation of the apparatus used to test the pumps with simulated collateral branches; and FIGS. 14a and b are diagrams showing comparative performances of the two pumps tested with a simulated collateral branch.

Figure 1A:
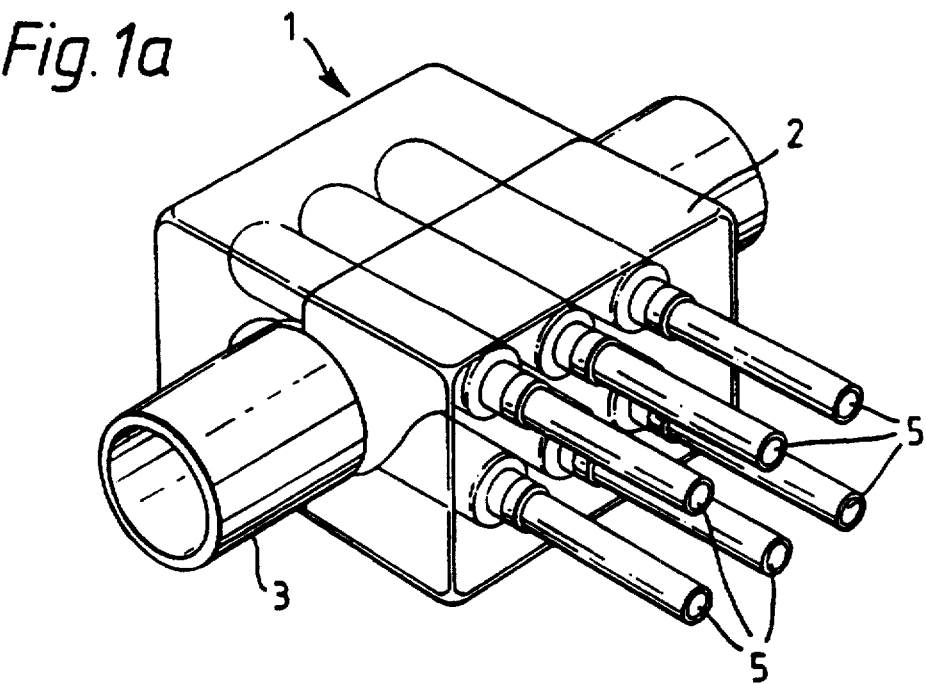
Figure 1B:
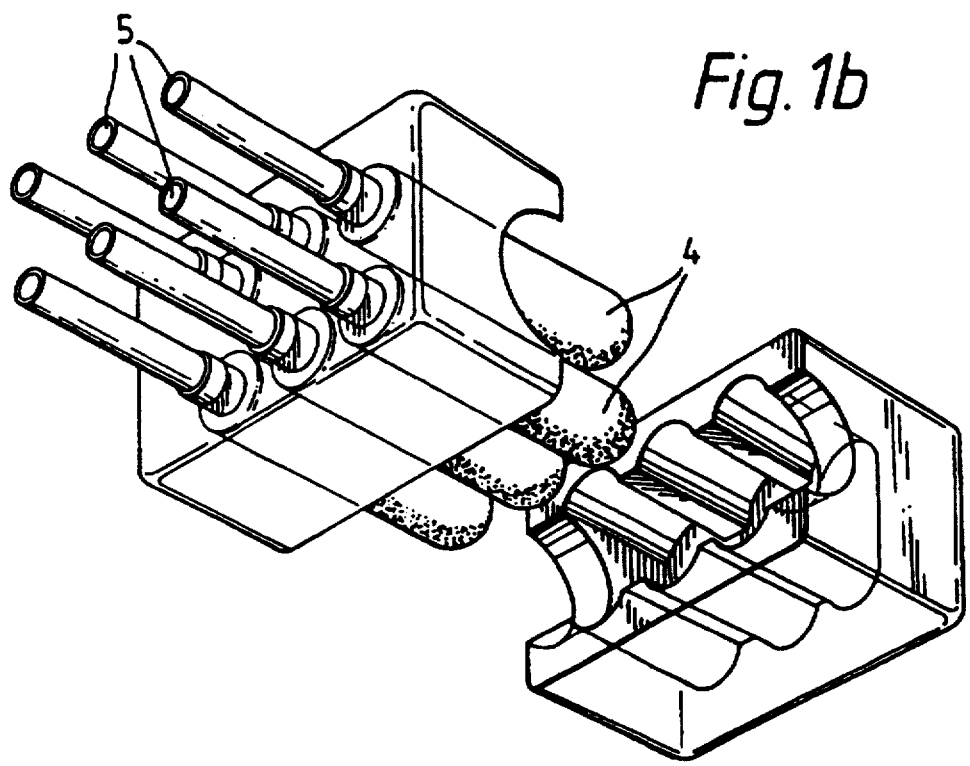
Figure 1C:
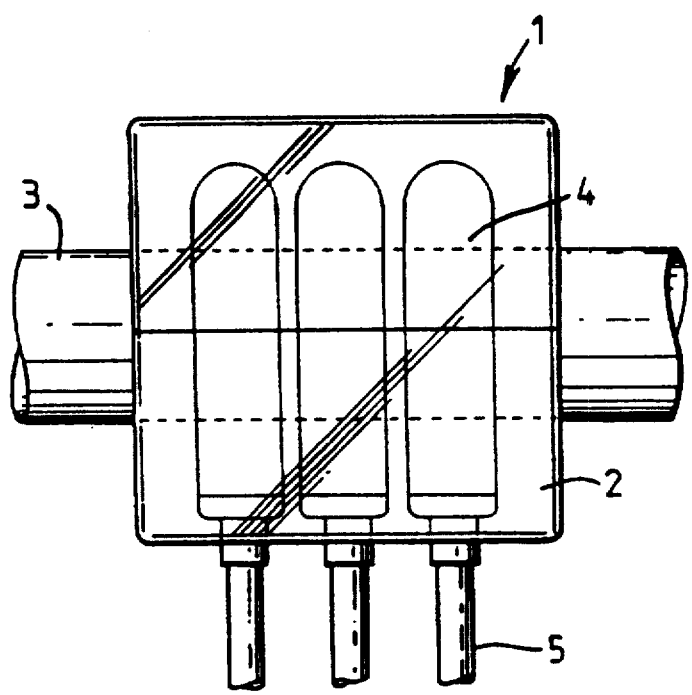
Figure 2A:
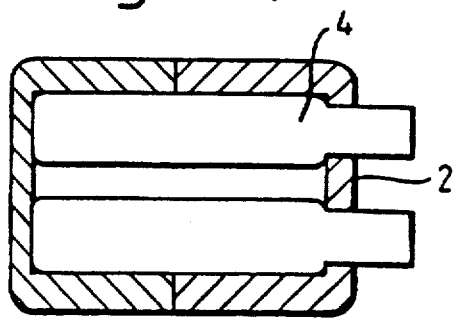
Figure 2B:
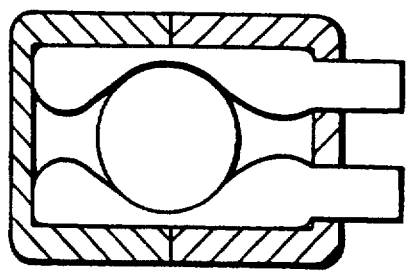
Figure 2C:
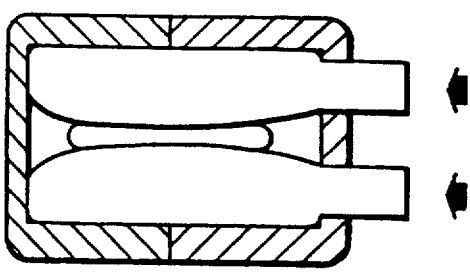
Figure 2D:
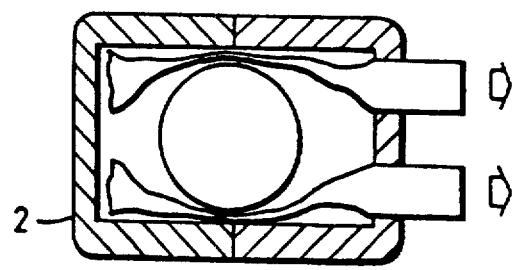

Referring first to FIG. 1, the pump 1 in accordance with the invention comprises a rigid casing 2 which annularly surrounds a vessel 3. The vessel 3 contains a liquid which is to be pumped by the pump 1. The casing 2 may be constructed of a rigid transparent plastics material, and is divided into two sections (FIG. 1a) so that it may be placed around the vessel 3. These two sections are then joined by means of a clip, bolt or other joining means. Housed inside the casing are two or more, and in this case three, pairs of parallel, inflatable ballonets 4. These ballonets 4 are constructed of a flexible plastics material and are connected to a pressure supply (not shown) by means of conduits 5. The pressure supply may be pneumatic or hydraulic, although pneumatic pressure is preferred as it has a faster response time and the amount of power dissipated in heat is less.

As shown in FIG. 2, the pair of ballonets 4 lies either side of the vessel 3 so that pressure passing through conduit 5 and into a ballonet causes inflation of the ballonets and hence constriction of the vessel 3. Conversely release of pressure from the ballonet causes the vessel to regain is shape. The release of pressure may be passive or by means of a vacuum pump.

Figure 3:
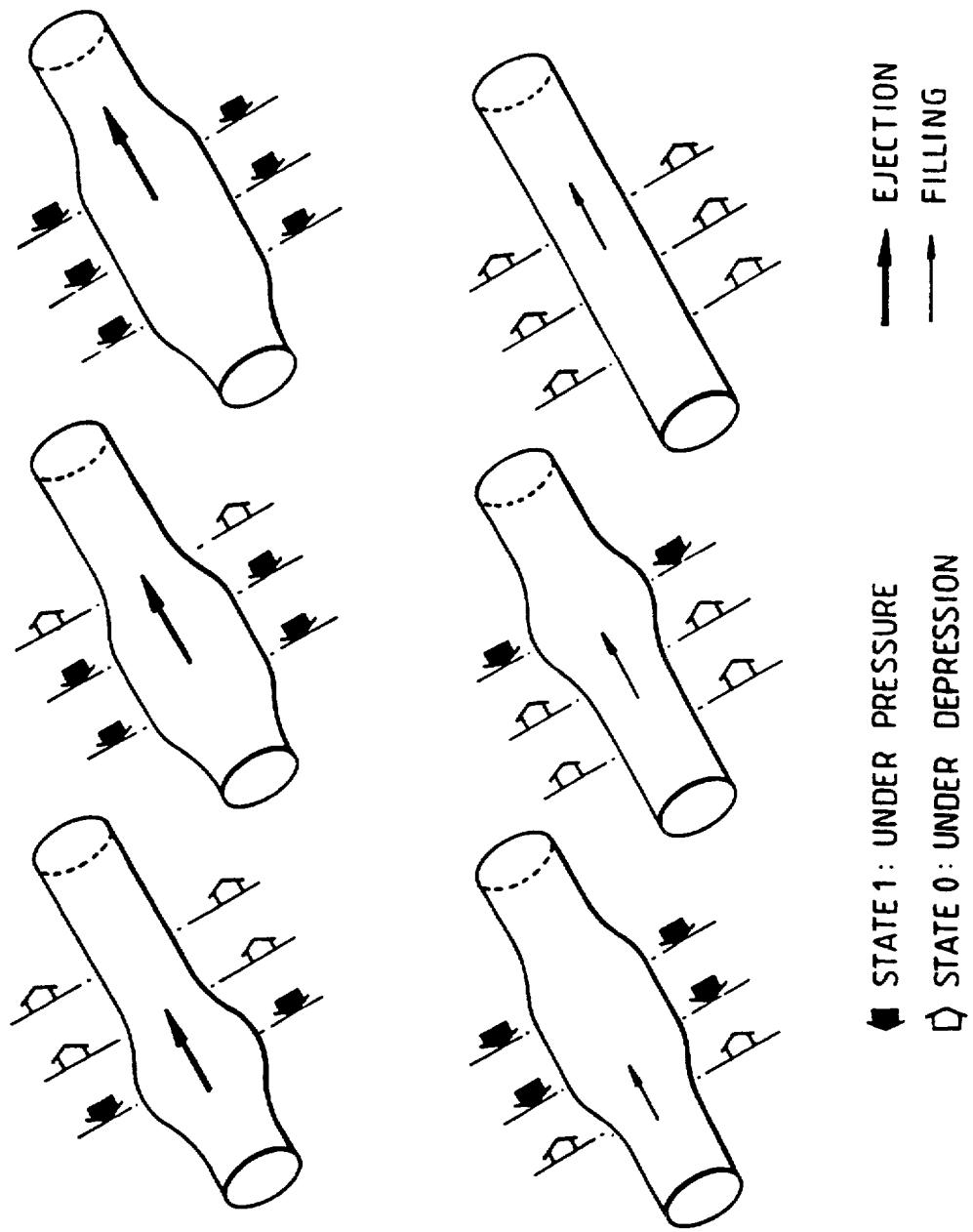
FIG. 3 shows a proposed sequence of dilation and constriction of the portal vein.

The pump has two or more pairs of ballonets 4 so that sequential inflation and deflation of each pair causes constriction of the vessel 3 and hence pumping of the liquid contained therein (FIG. 3).

Figure 4:
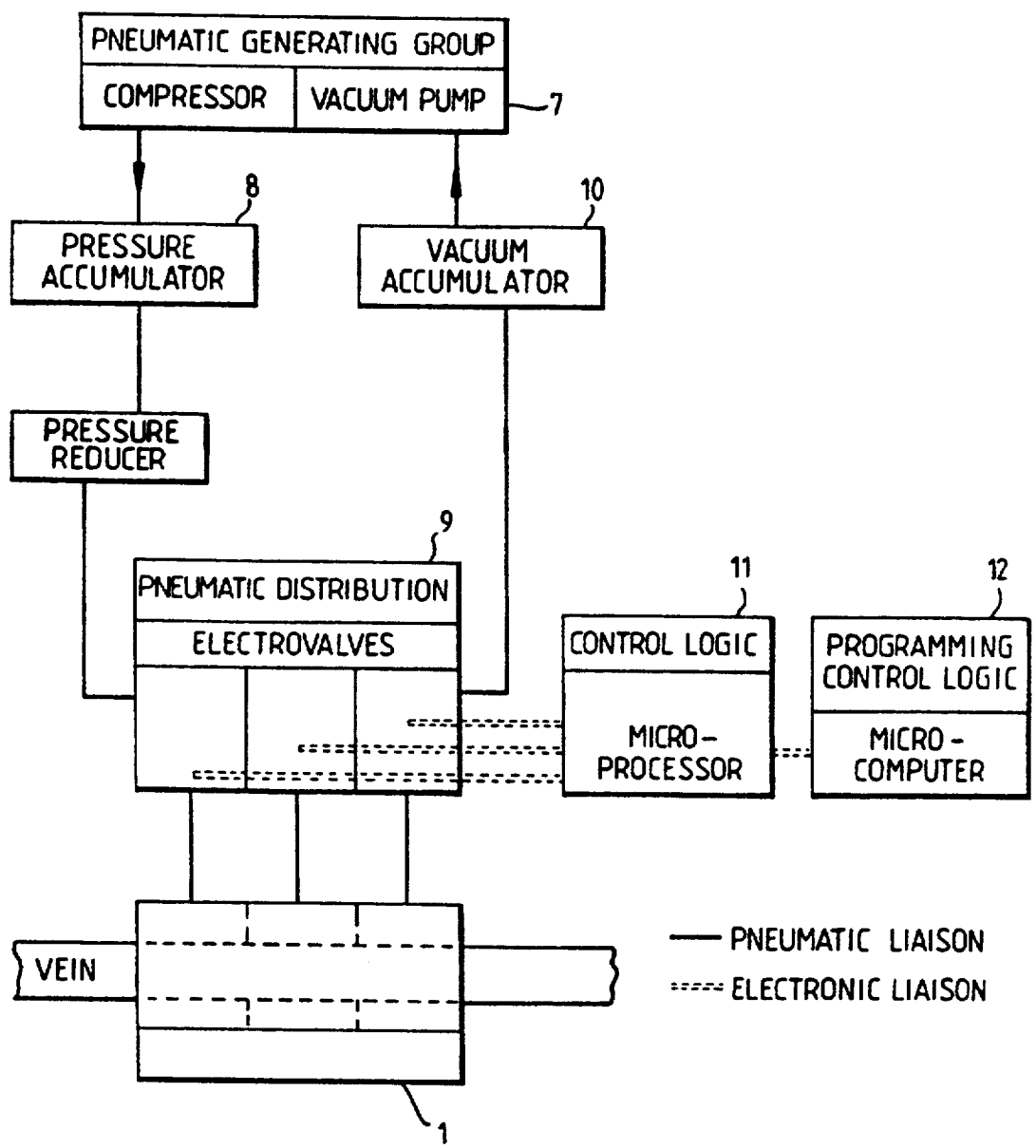
FIG. 4 shows schematically the control and power circuits in one embodiment of the invention.

Referring now to FIG. 4, the means by which the pump 1 can be regulated and controlled can be seen. Pressure generated by a compressor 7 is regulated by a pressure reducer 8 before entering the pump 1 via microelectrovalves 9. Deflation of the ballonets 4 is regulated by a vacuum accumulator 10 which ensures stabilised constant deflation. The microelectrovalves control the flow of fluid and are themselves under the control of a microprocessor 11 and a microcomputer/software 12. The microcomputer 12 is used to define the cycle of pressurisation and the microprocessor 11 monitors the electrovalves 9 so that an accurate cycle is achieved. Indeed, the period of the cycle may be between 0.251 seconds and 10 seconds with an accuracy of 1,000th of a second.

Inflation of the ballonets causes a progressive external compression of the vessel 3, and is hence particularly suited to assisting pumping of fluid in vessels such as veins, ducts and arteries. The use of the pump hereinafter will be described with reference to the hepatic portal vein, although it is to be understood that the invention is of general applicability and is not restricted to this specific area of use. As mentioned, the pump exerts a progressive external compression on a vessel which avoids injury to the venous wall and total venous occlusion which may be harmful. In use, the ballonets may be oblique to the flow of blood, or may preferably be perpendicular thereto.

The properties of a pump as described above can be characterised on a model of hepatic circulation. The portal vein is represented to scale by a conduit of flexible plastisol with an inner diameter of 20 mm and an outer diameter of 22 mm.

The performance of the pump is dependent on the following parameters:

| | |
|---|---|
| $\rho$ | density of liquid |
| $\mu$ | dynamic viscosity of liquid |
| $g = 9.81$ ms$^{-2}$ | acceleration in the field of gravity |
| $\Delta Q_v$ | change in output |
| $\Delta H$ | change in charge |
| $\Delta P = \rho \cdot g \cdot \Delta H$ | change in pressure |
| $R = \Delta P / \Delta Q_v$ | hydraulic resistance; in a rigid conduit of diameter d and length l, for a Newtonian fluid in laminar flow regime |
| $R = \dfrac{128 \cdot \mu \cdot l}{\pi \cdot d^{-4}}$ | |
| $P = \rho \cdot g \cdot \Delta Q_v \cdot \Delta H$ or $P = \Delta Q_v \cdot \Delta P$ | useful power transferred by the accelerator to the flow. |

In the tests, water is used instead of blood because their densities ($\rho$) are very similar (water = 1000 kg/m$^3$, blood = 1060 kg/m$^3$). This similarity means that the transferred energy is substantially the same for both liquids, but it is assumed that a) that output and hydraulic pressure have the same nominal values as in physiological conditions, and b) that hydraulic and venous resistance are the same. Hence the hepatic vascular bed can be simulated to test the pump, although the effect of hepatic arterial circulation, the phenomena of compliance and of opening of areas in the resistive bed, and the behaviour of non-Newtonian blood in the capillaries cannot be simulated.

Figure 5:
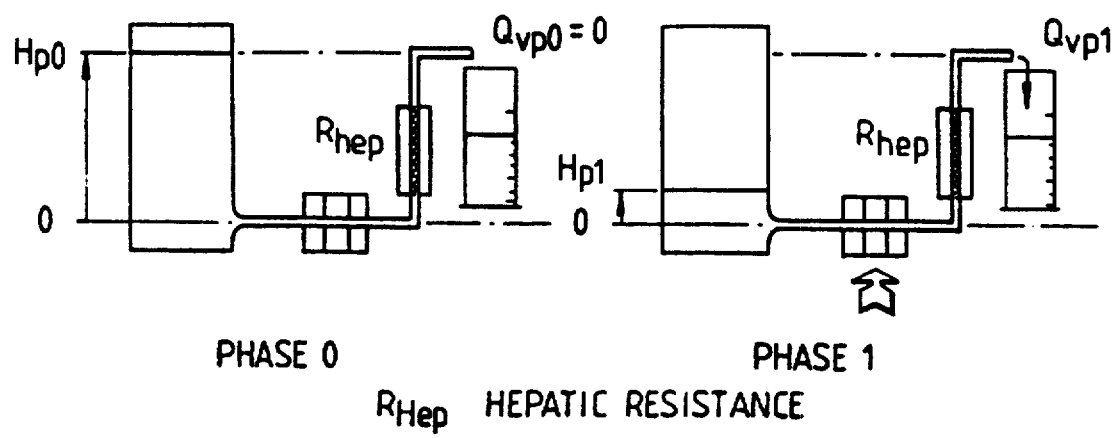
FIG. 5 shows a diagrammatic representation of apparatus used to define the direction of flow of liquid when pumped by a pump in accordance with the invention.

FIG. 5 shows diagrammatically apparatus used to define various characteristics of the pump. In particular the direction of flow of water can be seen by the use of coloured liquid tracers injected into the apparatus upstream of the pump and the output can be calculated precisely by the time taken to fill a standard volume.

The following describes experiments and results obtained in a comparative study of the performance of two pumps each with three pairs of ballonets but varying in their size, the first (A) being larger than the second (B). As mentioned, FIG. 5 shows diagrammatically apparatus used, in this case, to determine the direction of flow of water with and without the action of the pump. In Phase 0, without a pressure gradient between one end of the circuit and the other, the portal output ($Q_{vpo}$) is nil. With the pump functioning, as shown in Phase 1, water flows towards the area of hepatic resistance ($R_{hep}$), despite the resistance to flow being greater in this direction.

Figure 6:
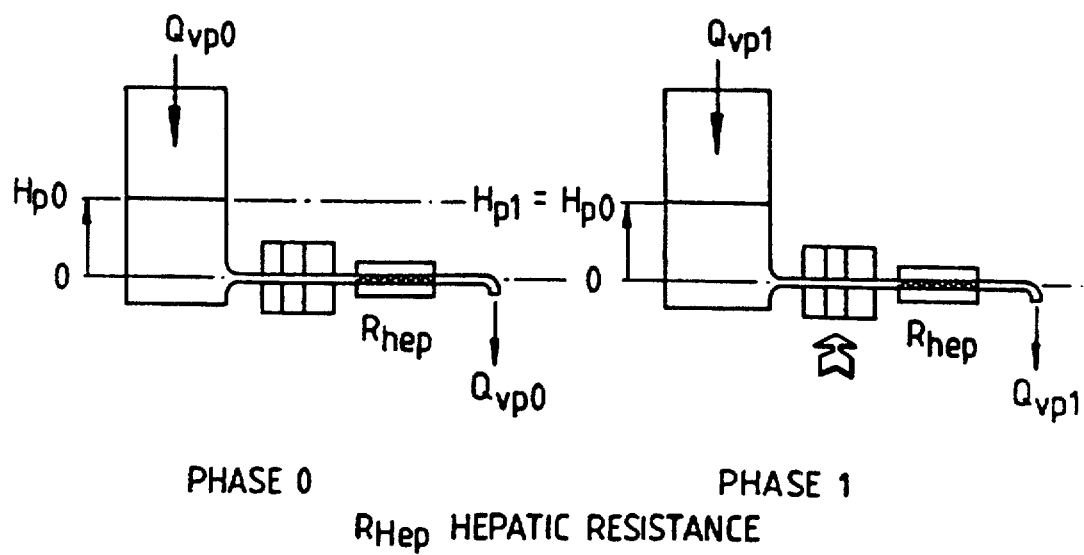
FIG. 6 shows a diagrammatic representation of apparatus used to define the increase in portal pressure for an increase in output for a pump in accordance with the invention.
Figure 7:
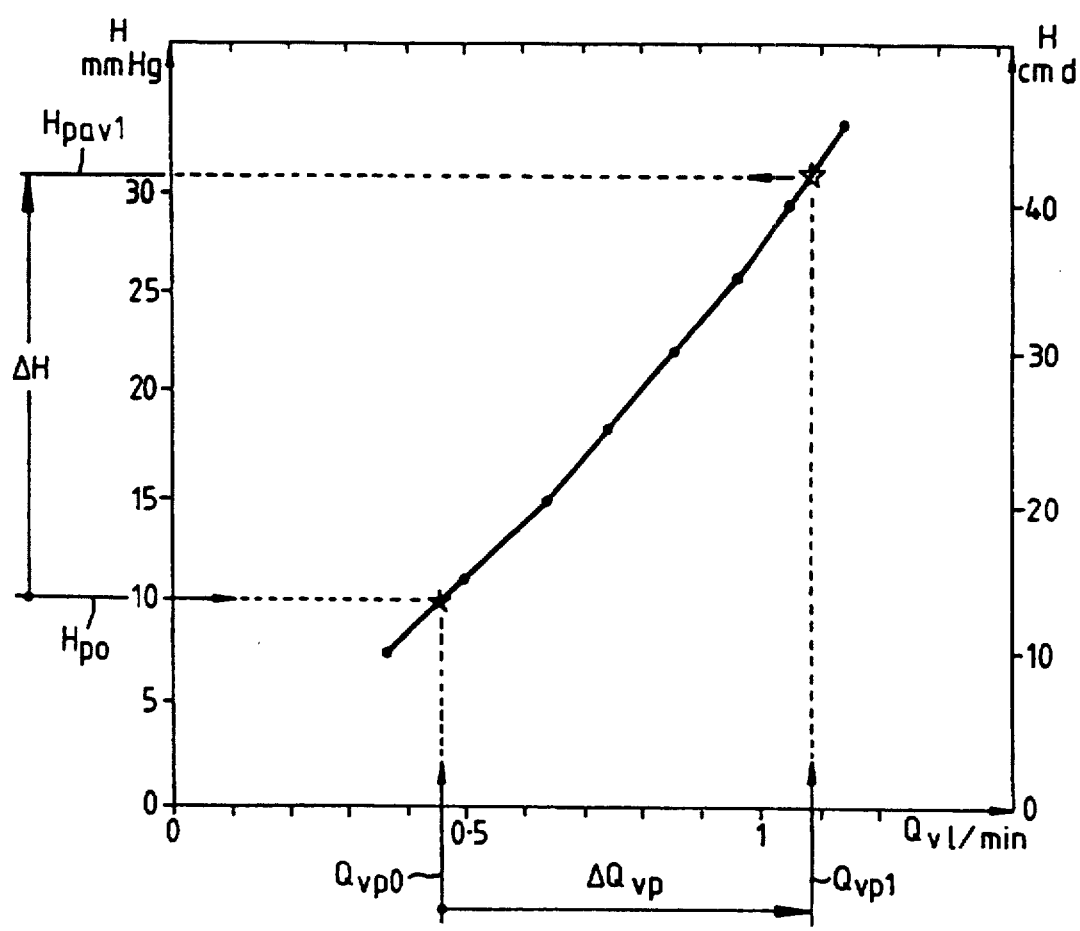
FIG. 7 is a graph showing output against portal pressure for the simulated hepatic bed, without action of a pump.
Figure 9A:
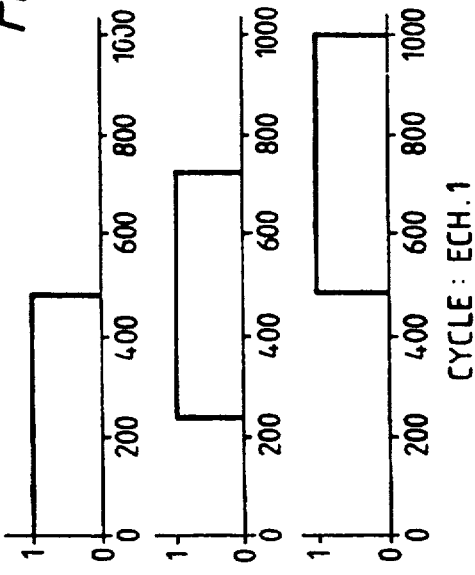
Figure 9B:
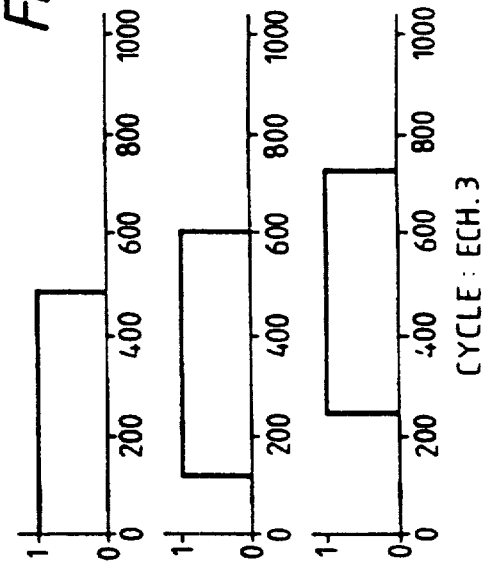
Figure 9C:
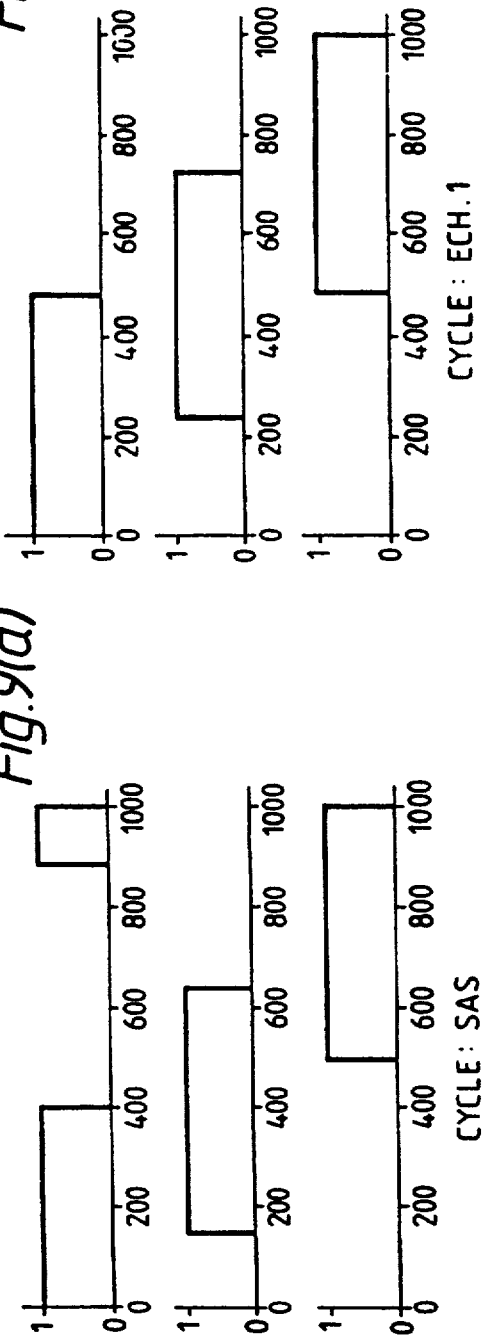
Figure 9D:
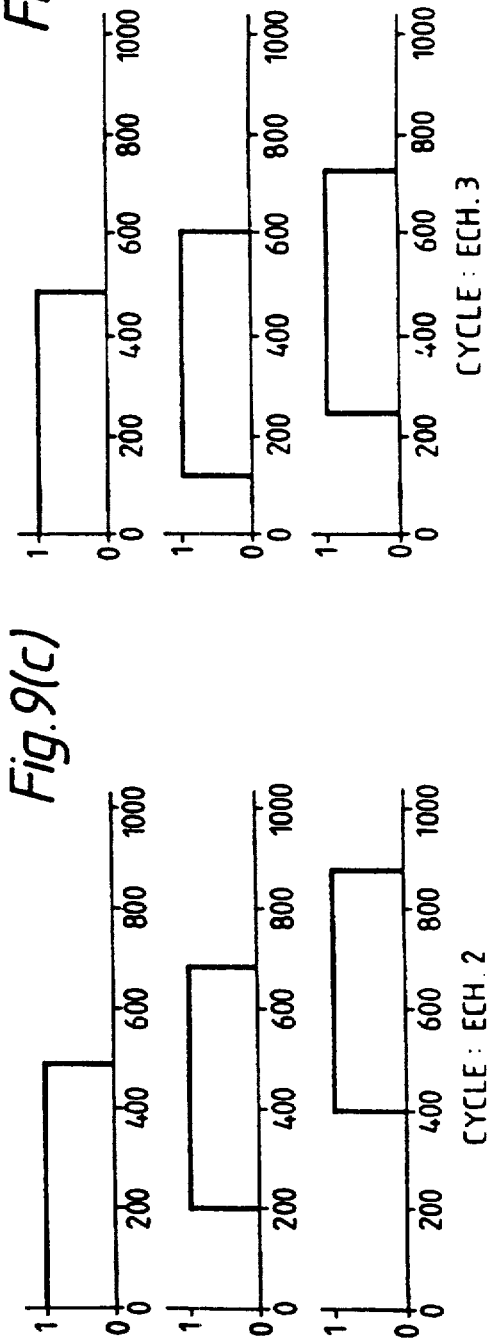

FIG. 6 shows apparatus used to find by how much output is increased by action of the pump. FIG. 7 shows how an increase in hepatic portal pressure $H_p$ affects an increase in output $Q_v$ without the pump being used. $H_{pav1}$ is the portal pressure which has to be generated for reestablishing output $Q_{vp1}$ with the pump at rest.

Referring now to FIGS. 8a and b, the effectiveness of the SAS and ECHELON type cycles can be assessed. As can be seen, the SAS cycle guarantees a one-way flow of liquid and prevents any backflow but has the disadvantage that it involves total venous occlusion, and hence the risk of venous wall damage. It also involves many sequences and can only transfer a low volume of liquid. The ECHELON type cycle cannot guarantee a prevention of backflow but propagates wave amplification without as many sequences of inflation and deflation or the need for venous occlusion. Chronographs of the various cycles tested are shown in FIG. 9, and FIG. 10a and 10b show a comparison of the performances of each of these cycles. As can be seen, the cycle ECH3 is more effective whatever the $H_{po}$ and $R_{hep}$ values. This cycle has therefore been retained for a further study of the characteristics of the pump.

The optimum period of cycle $T_m$, i.e. the length of time for a complete cycle as shown in FIG. 8b, can be found by varying the period of cycle T and examining the output $Q_{vp}$. FIG. 11 shows how the optimum period $T_m$ can be found for both pumps 1 and 2 by plotting period of cycle T against output $Q_{vp}$.

When $T_m$ is defined, the optimum speed of compression can be found by using the formula $$C_m = \frac{d}{T_m}$$

where d is the distance between the central axes of the ballonets. For both pumps, $C_m$ is virtually identical:

$$C_{m1} = \frac{22}{0.5} = 44 \text{ mms}^{-2}$$

$$C_{m2} = \frac{13}{0.3} = 43.3 \text{ mms}^{-2}$$

FIGS. 12a and b summarise the data contained in Table 1 below, for the two pumps tested on the simulation of hepatic circulation described.

TABLE 1

| phase 0 | | phase 1 | | | | | | |
|---|---|---|---|---|---|---|---|---|
| | | | | | $\Delta Q_{vp}$ | | | |
| $H_{p0}$ mm Hg | $Q_{vp0}$ l/min | Pump n* | $Q_{vp1}$ l/min | $\Delta Q_{vp}$ l/min | $\frac{Q_{vp0}}{\%}$ | $H_{pA V1}$ mm Hg | $\Delta H$ mm Hg | P mW |
| 10 | 0.65 | 1 | 1.12 | 0.47 | 72 | 20.4 | 10.4 | 11 |
|    |      | 2 | 1.32 | 0.675 | 104 | 25.5 | 15.5 | 23.3 |
| 22 | 0.50 | 1 | 0.84 | 0.34 | 68 | 46.4 | 24.4 | 18 |
|    |      | 2 | 0.80 | 0.30 | 60 | 41 | 19 | 13 |

It can be seen that the increase in portal output $\Delta Q_{vp}$ and maximum of transferred power P is obtained with low hypertension. $\Delta H$, the excess pressure applied increases with the hypertension.

Pump No. 2 is most efficient with moderate hypertension, although pump No. 1 is more efficient at higher hypertension.

Figure 14B:
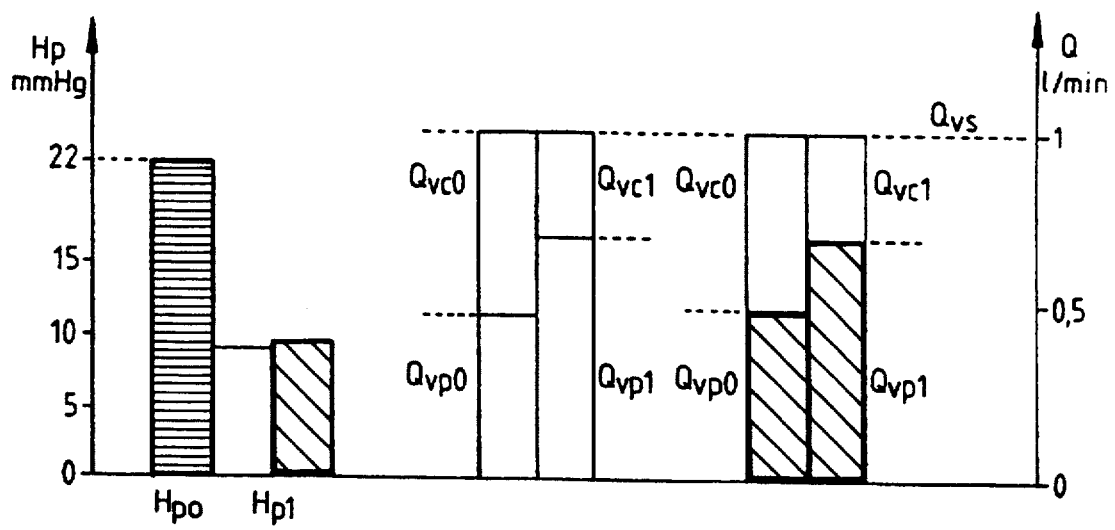

The performances of the two pumps may also be measured using a simulation of the collateral branch (simulating collateral circulation between the systemic and portal circulations). The apparatus used for this may be seen in FIG. 13, where a branch with collateral resistance $R_c$ is placed upstream of the pump. The results for pumps 1 and 2 can be seen both in Table 2 below and FIGS. 14a and 14b. Action the two pumps leads to increased portal output ($\Delta Q_{vp}$), decreased portal pressure ($\Delta H$) and decreased flow in the collateral ($\Delta Q_{vc}$).

TABLE 2

| phase 0 | | | | | phase 1 | | | | | | |
|---|---|---|---|---|---|---|---|---|---|---|---|
| $H_{p0}$ mm Hg | $Q_{vp0}$ l/min | Pump n* | $O_{vp0}$ l/min | $\Delta Q_{vc0}$ l/min | $H_{p1}$ mm Hg | $Q_{vs}$ l/min | $Q_{vp1}$ l/min | $Q_{vc1}$ l/min | $\Delta H$ mm Hg | $\Delta Q_{vp}$ l/min | $\Delta Q_{vc}$ l/min |
| 15 | 0.65 | 1 | 0.60 | 0.40 | 6.5 | 1 | 0.76 | 0.24 | −8.5 | +0.16 | −0.16 |
|    |      | 2 | 0.64 | 0.36 | 5.9 | 1 | 0.81 | 0.19 | −9.1 | +0.17 | −0.17 |
| 22 | 0.50 | 1 | 0.48 | 0.52 | 9.2 | 1 | 0.71 | 0.29 | −12.8 | +0.23 | −0.23 |
|    |      | 2 | 0.49 | 0.51 | 9.9 | 1 | 0.69 | 0.31 | −12.1 | +0.20 | 0.20 |

For both pumps the gain on portal output and decrease in portal pressure are accentuated with hypertension. Pump 2 is again more efficient at moderate hypertension and pump 1 is more efficient with high hypertension. However the difference between the efficiencies is minimal and the performance of the two pumps in these tests is very similar.

The invention may be further illustrated by means of the following examples:

Our new hypothesis is that it is possible to reduce the portal pressure in the oesophageal varices by increasing the portal blood flow across the cirrhotic liver. This would have the double advantage of preventing rebleeding without reducing the liver portal flow. To test this hypothesis we devised two experiments. The first (Example 1) was to investigate the relationship between portal pressure and liver portal flow in cirrhotic rat liver using the isolated liver perfusion model (Miller, L. L., Technique of liver perfusion. In: Bartosek, I., Guitani, A., Miller, L. L. eds. Isolated liver perfusion and its applications. New York: Raven Press, 1973: 11–52). The second (Example 1a) was to assess the ability of a newly designed pump to improve liver portal flow and reduce splanchnic portal pressure in pigs.

EXAMPLE 1

Liver cirrhosis was induced in Sprague-Dawley rats by IP injection of 0.3 ml carbon tetrachloride in mineral oil, three times weekly for 8 weeks. Two weeks following the last injection, the rats were submitted to laparotomy and the portal pressure was recorded by direct puncture of the portal vein. The livers were removed and placed in a modified isolated perfused system where the perfusion pressure varied from 0 to 45 cm $H_2O$. The perfusion solution was the oxygenated ($O_2$ 95% and $CO_2$ 5%), heated (37° C.) Krebs-albumin solution (pH 7.40±0.05). The base-line portal flow was measured for 20 minutes during which the portal pressure applied was equal to that measured in vivo prior to the sacrifice of the animal. The portal flow was then measured in the normal and cirrhotic livers over a period of 35 minutes. The portal flow was measured for 15 minutes at a higher pressure of either 25 or 45 cm of $H_2O$. Cirrhosis was confirmed histologically. Statistical analyses were made with the unpaired Student's t-test.

In the normal control rats (n=15), the base line portal pressure was 10.3±0.67 cm of $H_2O$. Subsequent increase of portal pressure to 25 cm of $H_2O$ in 10 of these rats increased the portal flow from 3.38±0.86 ml/min.gm$^{-1}$ to 6.25±1.2 ml/min.gm$^{-1}$ (P<0.001) while increase of portal pressure to 45 cm of $H_2O$ in the other 5 rats increased the portal flow from 2.23±0.42 ml/min.gm$^{-1}$ to 10.42±1.42 ml/min.gm$^{-1}$ (P<0.001).

In the cirrhotic rats (n=14), the base line portal pressure was 13.1±2.41 cm of $H_2O$. It was significantly (P<0.001) increased compared to the baseline portal pressure in normal rats. Increase of portal pressure to 25 cm $H_2O$ in six of these rats increased the portal flow from 2.32±0.75 to 3.97±1.29 ml/min.gm$^{-1}$ (P>0.05) while increasing the portal pressure to 45 cm of $H_20$ in the other four rats caused a rise in portal flow from 1.64±0.32 to 4.50±1.18 ml/min.gm$^{-1}$ (P<0.001). Histological examination of the normal and cirrhotic livers showed no parenchymal damage following increased portal pressure.

In the normal liver the doubling of portal pressure was associated with a doubling of portal flow (105% and 360% increase in portal pressure was associated with a 91% and 383% increase in portal flow respectively). In the cirrhotic liver, there was a similar direct relationship (i.e. 88% and 215% increase in portal pressure was associated with a 72% and 178% increase in portal flow respectively).

Therefore in both normal and cirrhotic liver, increase portal pressure was associated with a significant increase in portal flow.

EXAMPLE 1a

Two 70 kg pigs were anaesthetized and submitted to laparotomy. Via a bilateral subcostal incision the portal vein was dissected. The portal pressure was recorded with the insertion of a cannula in a jejunal vein. Another catheter was introduced via another jejunal vein and advanced beyond the portal vein bifurcation. The portal flow was measured continuously with Gould-Stratham 2202 flow meter using a probe placed around the main left branch of the portal vein. Following this, the branches of the portal vein were dissected. All the right and one left segmental portal branches were ligated. This raised the portal pressure in the first pig from 13 to 24 mm Hg and in the second pig from 12 to 23 mm Hg. It also reduced the liver portal flow from 950 to 700 ml/min in the first pig and from 650 to 180 ml/min in the second pig.

At this stage, a pump in accordance with one aspect of the present invention was applied around the portal vein. The pump consisted of an air driven pump composed of three pairs of balloons enveloped by a rigid box. The three pairs worked in a cyclical sequence controlled by computer. The length, width and height of the balloon were 35 mm, 11 mm and 10 mm, respectively. The cycle duration was 0.8 second. The pressure in the balloons was generated with a compression-vacuum generator with an applied pressure of 0.32 bar.

Measurements of portal pressures and liver portal flow were repeated in both pigs with successive applications of the pump. Statistical analysis were made with paired t-test.

Five successive activations of the pump in the first pig reduced the splanchnic portal pressure from $23.7 \pm 1.09$ mm to $19.7 \pm 0.67$ mm Hg (downstream of the pump) ($P < 0.01$) and increased the portal pressure upstream of the pump from $23.88 \pm 0.54$ mm to $31.24 \pm 2.54$ mm Hg. This was associated with an increase in portal flow from $693 \pm 11$ to $842 \pm 13$ ml/min ($P < 0.001$). In the second pig, activation of the pump reduced the splanchnic portal pressure (downstream of the pump) from $21.75 \pm 1.5$ to $18.5 \pm 1.29$ mm Hg and increased the portal pressure upstream to the pump from $21.5 \pm 1.91$ to $24.5 \pm 2.51$ mm Hg ($P < 0.05$). This was associated with an increase in portal flow from $215 \pm 73$ to $280 \pm 70$ ml/min ($P < 0.001$).

Our in vitro study shows that increased portal pressure leads to increased portal flow. This was observed in both normal and cirrhotic liver using the isolated perfused model. Conventional histological examination of these livers did not reveal any parenchymal damage following brief periods of increased portal pressures.

In the reported in vivo experiments in pigs (Example 1a) with portal hypertension, the pump reduced the splanchnic portal pressure and simultaneously increased the portal liver flow.

I claim:

1. A method of treating the hepatic portal vein or hepatic pedicle to improve the blood flow therethrough against increased impedance caused by abnormality of the liver, said method comprising the steps of:
   placing a pump in communication with the hepatic portal vein or hepatic pedicle; and
   actuating said pump to improve blood flow through said hepatic portal vein or hepatic pedicle and thereby improve blood flow through the liver.

2. A method as claimed in claim 1, wherein said pump is an Archimedes screw pump.

3. A method as claimed in claim 1, wherein said pump is a peristaltic-type pump.

4. A method as claimed in claim 2, wherein said Archimedes screw pump is located within a prosthesis which is inserted into or grafted between sections of said hepatic portal vein.

5. A method as claimed claim 3, wherein said peristaltic-type pump generates its peristaltic effect by a roller action.

6. A method as claimed claim 3, wherein said peristaltic-type pump uses hydraulic or pneumatic power to generate its peristaltic effect.

7. A method as claimed in claim 6, wherein said peristaltic type pump uses pneumatic power provided via an air compressor located outside the body of the patient.

8. A method as claimed claim 6, wherein said peristaltic-type pump comprises a jacket, sheath or collar which surrounds said hepatic portal vein.

9. A method as claimed in claim 8, wherein said jacket, sheath or collar is divided into three annular compartments, and wherein each of said compartments is supplied independently with its own pneumatic or hydraulic supply.

10. A method as claimed in claim 9, wherein said compartments are inflated and deflated sequentially as shown by the following table, compartment 1 being the distal and compartment 3 being the most proximal with respect to said area of impedance, D indicating deflation and I indicating inflation:

| Compartment | Time | | | | |
| --- | --- | --- | --- | --- | --- |
| | $t_1$ | $t_2$ | $t_3$ | $t_4$ | $t_5$ |
| 1 | I | I | D | D | I |
| 2 | D | I | I | D | D |
| 3 | D | D | I | D | D |

11. A method as claimed in claim 1, wherein a section of said blood vessel is removed and replaced by a jacket, sheath or collar, and blood is caused to flow by the combination of inflation of said jacket, sheath or collar and one-way valves at both ends of the jacket.

12. A method as claimed in claim 1, wherein operation of said pump is controlled by a microprocessor.

13. A method as claimed in claim 12, wherein said microprocessor is located at skin level close to the site of the blood vessel.

14. A method as claimed in claim 12, wherein said microprocessor is located externally in a housing.

15. A method as claimed in claim 1, wherein the pressure in said blood vessel either side of said pump is monitored by means of first and second sensors, said first sensor being located so as to sense the prevailing pressure in that segment of said blood vessel upstream of said pump and said second sensor being located so as to sense the prevailing pressure in that segment of said blood vessel downstream of said pump.

16. A method as claimed in claim 15, wherein said first and second sensors are connected to said microprocessor so as to control the action of said pump within preset pressure limits.

17. A method as claimed in claim 1, wherein said abnormality of the liver is cirrhosis of the liver, liver insufficiency or atherosclerosis of the renal artery.

18. A method as claimed in claim 2, wherein said pump is housed in a prosthesis which is inserted into the hepatic portal vein.

19. A method as claimed in claim 2, wherein said pump is housed in a prosthesis which is grafted between sections of the hepatic portal vein.

20. A method as claimed in claim 1, wherein said pump is placed in or around the hepatic portal vein or hepatic pedicle.

21. A method as claimed in claim 1, wherein said pump comprises a housing means for annularly surrounding said hepatic portal vein, said housing means containing a plurality of flexible, inflatable containers mounted for contact with said hepatic portal vein and means for effecting sequential inflation and deflation of said containers so as to create a peristaltic pumping effect.

22. A method as claimed in claim 21, wherein said housing means is divided parallel to the direction of said flow of blood so that it, may be placed around said hepatic portal vein.

23. A method as claimed in claim 21, wherein said means for sequential inflation and deflation comprises a pressure source, a pressure regulator, a microprocessor and a microcomputer.

24. A method as claimed in claim 23, wherein said means for sequential inflation and deflation further comprises microelectro valves.

25. A method as claimed in claim 22, wherein said housing means is formed of a substantially rigid plastic material.

26. A method as claimed in claim 21, wherein said containers are formed of a substantially extendable plastic material.

27. A method as claimed in claim 21, wherein said containers lie parallel to one another and perpendicular to the direction of said blood flow.

* * * * *